United States Patent [19]

Britton

[11] Patent Number: 4,644,285
[45] Date of Patent: Feb. 17, 1987

[54] METHOD AND APPARATUS FOR DIRECT MEASUREMENT OF CURRENT DENSITY

[75] Inventor: James N. Britton, Houston, Tex.

[73] Assignee: Wayne Graham & Associates International, Inc., Houston, Tex.

[21] Appl. No.: 658,612

[22] Filed: Oct. 9, 1984

[51] Int. Cl.⁴ .................................... G01N 27/42
[52] U.S. Cl. .................................. 324/425; 324/439; 204/147; 204/196; 204/404; 204/400; 204/1 T
[58] Field of Search ................. 324/425, 439, 248, 72, 324/72.5, 71 E; 204/147, 196, 400, 1 T, 404; 307/95

[56] References Cited

U.S. PATENT DOCUMENTS

| | | |
|---|---|---|
| 2,780,781 | 2/1957 | Medlar . |
| 2,795,759 | 6/1957 | Rezek . |
| 2,802,182 | 8/1957 | Godshalk et al. . |
| 2,832,046 | 4/1958 | Rezek . |
| 2,869,071 | 1/1959 | Esterson . |
| 3,054,946 | 9/1962 | Esterson . |
| 3,649,492 | 3/1972 | Marsh . |
| 4,134,059 | 1/1979 | Stankoff ..................... 324/439 X |
| 4,351,703 | 9/1982 | Winslow . |
| 4,489,277 | 12/1984 | Goolsby .......................... 324/425 |

OTHER PUBLICATIONS

A. D. Goolsby, "The Results of Monitoring Platform ELLEN Cathodic Protection for Two Years", *Materials Performance*, Apr. 1984.

Primary Examiner—Reinhard J. Eisenzopf
Assistant Examiner—Robert W. Mueller
Attorney, Agent, or Firm—Darryl M. Springs

[57] ABSTRACT

In a cathodic protection system for protecting a metal structure in contact with a surrounding electrolytic medium, method and apparatus are provided for directly measuring current density. A small metal sample cathode of a like material as the metal structure having a predetermined surface area exposed to the electrolytic medium is located adjacent the surface of the metal structure. A direct electrical path is completed between the sample cathode and the metal structure that is substantially IR free. At least a portion of the electrical path between the sample cathode and the metal structure is insulated from the surrounding electrolytic medium and the metal structure. A voltage directly proportional to the current passing through the electrical path is generated by disposing a toroidal coil in the insulated space by detecting the flux field associated with the current flow through the sample cathode.

57 Claims, 13 Drawing Figures

METHOD AND APPARATUS FOR DIRECT MEASUREMENT OF CURRENT DENSITY

BACKGROUND OF THE INVENTION

This invention generally relates to measuring current density in electrochemical processes, and more particularly relates to methods and apparatus for directly measuring current density in cathodic protection systems for the protection of large metal structures in contact with an electrolytic medium against corrosion attack. More particularly, this invention relates to methods and apparatus for directly measuring current density in any portion of a metal structure, even those having a complex geometric design and configuration, in contact with an electrolytic medium and protected by a cathodic protection system.

Large metal structures located in land or sea regions, such as pipelines, wells, structural supports, offshore drilling platforms, ship hulls, metal supports and framing under or imbedded in concrete, and the like, when exposed to a corrosive electrolytic environment tend to be corrosively destroyed over a period of time. To minimize this corrosive attack, many means have been utilized to safeguard the metal surfaces in contact with the corrosive electrolytic environment.

One such approach is to cover the metal structure with protective materials, such as inert wrappings of fiber or cloth, and exterior impervious coatings of bituminous materials, cement, epoxy resins and the like. Unfortunately, it is difficult to spread the protective coatings evenly during their application, or voids are created during the installation of the structure within the earth or sea region or thereafter by mechanical damage or injury to the structure and protective coating. The exposed surfaces of the structure are then exposed to the corrossive electrolytic environment.

Many schemes have been devised for protecting these structures. For example, cathodic protection systems have been developed for mitigating the corrosion of submarine or subterranean metal structures by connecting sacrificial anodes of a metal higher in the electromotive series than the metal of the structure, such as magnesium or zinc in the case of ferrous structures, to the structure and disposing them within the electrolytic environment or medium. Also, direct current electricity can be supplied to the structure to provide all or part of the current required for cathodic protection. Less expensive anodic metals, such as graphite, can also be utilized as anodes for an auxiliary current source as used to drive current from the anode to the structure being protected. Cathodic protection of the structure is achieved when cathodic areas of the structure receive all electrons utilized in the cathodic process from the auxiliary anode, and not from the local anodes of the structure itself.

In either of the above two events, the flow of cathodic current from the anode to the metallic structure is assumed to be of proper magnitude when the structure (steel) is about 0.80 to 1.00 volts negative relative to the earth region or medium immediately surrounding the structure as measured with respect to a silver-silver chloride reference electrode. Under these conditions, the structure may be directly exposed to the earth formation or sea water and all of its portions are protected against corrosion attack. The shift in cathode potential is proportional to the current density (mA/ft$^2$) applied to the cathode. The desired current density (mA/ft$^2$) for protecting offshore structures generally falls in the range of 1 mA/ft$^2$ to 50 mA/ft$^2$. However, a typical range for most structures is 5–10 mA/ft$^2$. The current density required to move the potential into the protective non-corroding range varies widely with the grade of steel of the cathode, the electrolytic composition, temperature, pressure, flow rate of the electrolytic medium in sub-sea situations, etc. It is therefore desirable to be able to measure the current density accurately even if all of the factors are not known.

Many methods and arrangements have been proposed for evaluating the cathodic protection of a metal structure. Generally, these techniques only measure the potential of the structure in the earth region relative to a closely spaced adjacent reference electrode, such as the copper sulfate half-cell, or the silver-silver chloride reference electrode. Other techniques have been developed that monitor or measure the current passing into the anodes from the anode power supplies, and, assuming that all of the current flow is impressed upon the metal structure, an approximation of the current density may be calculated based on an approximation of the total surface area of the structure to be protected. However, this technique is only an approximation of the current density and it is known that the current density is not uniform over the entire structure surface.

Other techniques utilize a sample cathode spaced from and insulated from the metal structure and through which a "measurement" of the current impressed upon the sample cathode is made by means of determining the IR drop in a milliohm impedance shunt circuit. However, the accuracy of such a measurement is not reliable, because very low currents are hard to measure with any reliability when using such a low resistance shunt, and because low currents or current densities require a large cathode area, often 10–12 ft$^2$ which has to remain perfectly insulated from the cathode. In a sea water environment, it is difficult to maintain the insulation intact when it is immersed in the seawater for a long time period.

In addition, no matter how accurate the actual readings of the current through the sample cathode are, since the current density determination is made by approximating the surface area of the metal structure, large errors can often result because of the difficulty in calculating the correct surface area of the many complex geometric configurations of certain structures, such as offshore oil well platforms and the like. In addition, it is well known that, because of the complex geometric configurations of certain structures, the current density is not uniform over the entire structure.

The monitoring and evaluation of cathodic protection systems of metal structures has been limited in the past by the inability to directly measure current density at any selected location on the surface of the structure. All attempts to measure current density have had to be confined to large areas because of the reasons previously outlined. Therefore, it has not been possible to monitor current density at what is essentially a "spot" location, which could be located in a confined area or shielded area of complex structure.

The present invention provides a method for directly measuring current density at any location on the surface of a metal structure protected by a cathodic protection system. The measuring apparatus is compact and may be installed in virtually any location on the surface of a metal structure, even including recesses and joints and shielded areas of structures having complex geometric configurations.

BRIEF SUMMARY OF THE INVENTION

In accordance with this invention, a method of directly measuring current density at the surface of a metal structure in contact with a surrounding electrolytic medium and protected by a cathodic protection system is disclosed. The steps include locating adjacent to the surface of the metal structure a small sample cathode of a like material as the metal structure and having a predetermined surface area exposed to the electrolytic medium and completing a direct electrical path that is substantially IR free between the sample cathode and the metal structure. Additional steps include insulating from the surrounding electrolytic medium between the sample cathode and the metal structure at least a portion of the electrical path passing therethrough and detecting the magnetic flux field associated with the current flow through the sample cathode and the insulated portion of the connecting electrical path impressed by the cathodic protection system, and generating a signal directly proportional to the detected current flow through the sample cathode and the connecting electrical path.

The apparatus for accomplishing the direct current density measurement comprises a sample cathode constructed of a like material as the metal structure and having a predetermined surface area exposed to the electrolytic medium, the sample cathode being located in an adjacent relationship to the surface of the metal structure. A box-like housing having one open end receives the sample cathode, with the sample cathode surface exposed to the electrolytic medium substantially closing the open end of the housing member. A sealing material is disposed between the sample cathode and the interior walls of the box-like housing member to seal and insulate the space between the sample cathode and the housing member to form a sealed chamber.

A connecting means that is substantially IR free is provided between the sample cathode and the metal structure for completing a direct electrical path between the sample cathode and the metal structure, with at least a portion of the connecting means passing through the sealed chamber. A non-intrusive current measuring means is disposed within the sealed chamber and cooperates with the portion of the connecting means passing through the chamber. The current measuring means detects the magnetic flux field associated with the current flow through the sample cathode and the connecting means that is impressed by the cathodic protection system. The current measuring means generates a voltage signal directly proportional to the measured current. Since the surface area of the sample cathode is precisely predetermined, and the generated voltage signal is directly proportional to the detected current passing through the connecting means, the voltage output may be calibrated to present a reading directly representative of the current density of the cathodic protection current impressed on the sample cathode.

The connecting means may comprise a cathode connector rod constructed of a metal providing a substantially IR free electrical path, one end of which is attached to the sample cathode and in electrical contact therewith, the other end of the rod adapted for attachment to the metal structure and in electrical contact therewith to establish a substantially IR free electrical path between the sample cathode and the metal structure, and a contacting means cooperating with the other end of the cathode connector rod for establishing electrical contact with the surface of the metal structure. The resistance of the connecting means is so low, generally on the order of $5.0-8.0 \times 10^{-6}$ ohms, that the IR drop is substantially zero, enabling the current to be accurately measured down to extremely small values. In a fixed unit, the contacting means may comprise a mounting bracket constructed of a metal providing a substantially IR free electrical path and adapted for being fastened to the surface of the metal structure and making electrical contact therewith. The mounting bracket is further adapted for mounting the other end of the cathode connector rod in electrical contact therewith. In a portable, hand-held device, the contacting means may comprise a sharp, conically-pointed tip attached to the other end of the cathode connector rod for making direct electrical contact with the metal structure when the tip is forced against the surface of the structure.

In a preferred embodiment, the non-intrusive current measuring means comprises a power supply for furnishing a predetermined voltage, a saturable toroidal core disposed in the sealed chamber and cooperating with the portion of the cathode connector rod passing through the chamber, and a cable electrically interconnecting the toroidal core and the power supply. The toroidal core, when excited by the power supply voltage, detects the magnetic flux field associated with the cathodic protection system current impressed on the sample cathode and flowing through the cathode connector rod. The toroidal core generates an output voltage signal directly proportional to the detected or measured current.

One primary advantage of the present invention is that the current sensing apparatus is small and can be fixed to the structure at any convenient location, or it can be made portable and used by divers or other means for putting the apparatus in direct contact with the surface of the metal structure to determine current density at a specific selected location.

Another advantage of the present invention is that the detection means allows a direct reading to be obtained of current density.

Yet another advantage of the present invention is that the current measurement is performed by non-intrusive current measuring means that need not be directly connected to the cathode or conductor carrying the cathode impressed current.

BRIEF DESCRIPTION OF THE DRAWINGS

In order that the manner in which the above-recited advantages and features of the invention are achieved can be understood in detail, a more particular description of the invention will now be made by reference to specific embodiments thereof which are illustrated in the accompanying drawings, which drawings form a part of this specification.

In the drawings.

DETAILED DESCRIPTION OF THE INVENTION

The description which follows will generally describe the use of the invention with particular reference to utilizing the current density measuring apparatus as mounted on a subsea metal structure, such as an offshore drilling platform, a production platform or the like. However, it should be noted that the details of the method and apparatus hereinafter described will equally applicable for the direct measurement of current density in many other applications, such as docks, jetties, and harbors, fresh water metal tanks in contact with the earth's surface, crude oil storage tanks, buried pipelines, ballast tanks, process vessels, well casings, ships hulls, and plating tanks used in electrolytic metal plating.

Figure 1:
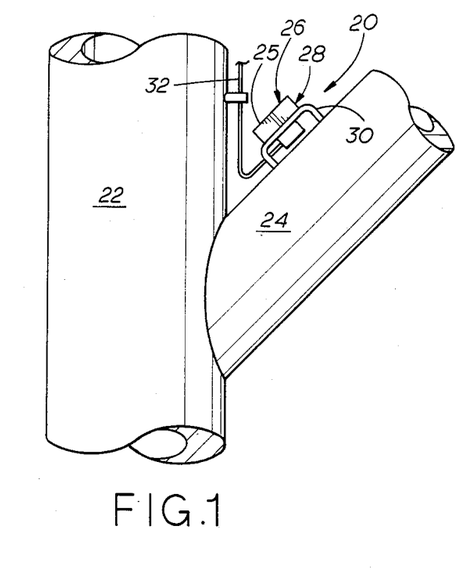
FIG. 1 is a partial side view in elevation of part of a metal structure, such as an offshore drilling platform, showing a typical location of the current density monitoring apparatus according to this invention.
Figure 2:
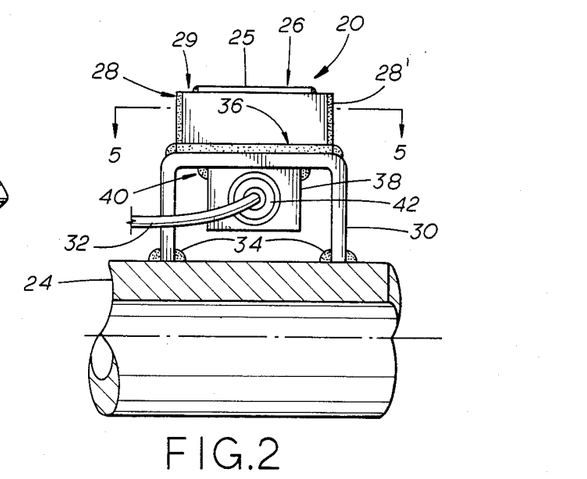
FIG. 2 is a side view in elevation of the current density monitoring apparatus according to the present invention shown mounted on a metal structure.
Figure 3:
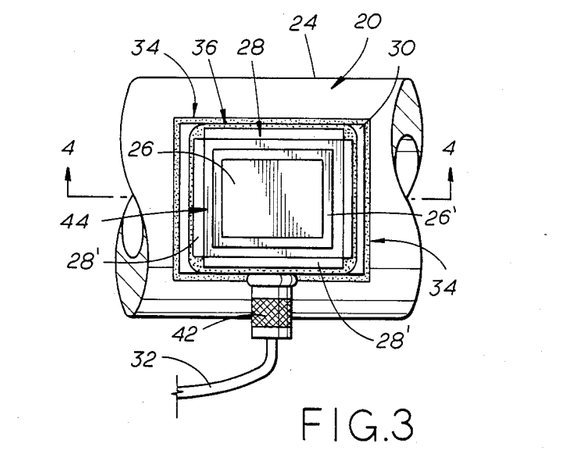
FIG. 3 is a plan view of the current density measuring apparatus according to the present invention shown mounted on a metal structure.

Referring now to FIG. 1, a current density measuring means 20 is shown mounted on an intersecting metal cross-brace 24 of an offshore platform, the cross-brace 24 being welded to or integrally attached to a main portion of the metal structure support 22. The current density measuring means 20 has a sample cathode 26 with an outer surface exposed to and in contact with the electrolytic medium, i.e., the sea water, and is sealingly housed in a pressure-proof housing 28 as will be hereinafter further described. The housing 28 is supported on a generally inverted U-shaped bracket 30 which functions as a portion of a substantially IR free electrical connection for connecting the sample cathode 26 to the metal structure 24, as will be hereinafter described in greater detail. A cable 32, having multiple conductors therein for purposes to be hereinafter further described, connects the current density measuring means 20 with a remote location, usually above sea level on the platform (not shown) for monitoring, recording and/or displaying the current density measurement information.

Referring now to FIGS. 1-5, the basic construction of the current density monitoring means 20 will be explained. The sample cathode 26 comprises a box-like structure having depending sidewalls 26' closed at the top by the sample cathode 26 with surface 25 in contact with the electrolytic medium, i.e., the sea water. The sample cathode 26 forms an inverted box-like member open on the bottom side for purposes to be hereinafter further described. A mounting or support bracket 30 having a generally inverted U-shape is mounted on the metal structure by appropriate mounting means to insure intimate electrical contact between the bracket 30 and metal structure 24, such as by welding as shown at 34. A housing member 28 having side walls 28' is mounted on the top surface 33 of the bracket 30 and attached thereto by means of welding or brazing as shown at 36. The walls 28' cooperate with the top surface 33 of bracket 30 to form the box-like housing member 28 having an open upper side.

The geometric configuration of the box-like housing member 28 is identical to the configuration of the inverted box-like sample cathode structure 26, but is slightly larger for receiving the sample cathode structure 26, but leaving a uniform and narrow space between the upstanding walls 28' of the housing member 28 and the depending walls 26' of the sample cathode 26. A steel cathode connection rod 54, constructed of a material for providing a substantially IR free electrical path, has one end connected to the inner surface 27 of the sample cathode 26 by means of brazing or welding 23. The other end of the cathode connector rod 54 is mounted in an aperature in the upper surface 33 of the mounting bracket 30, and also constructed of a meterial for providing a substantially IR free electrical path, fixed thereto by welding as at 55. The cathode connector rod 54 is sized to space the sample cathode 26 from the surface 33 of the mounting bracket 30 for purposes to be hereinafter further described.

Figure 4:
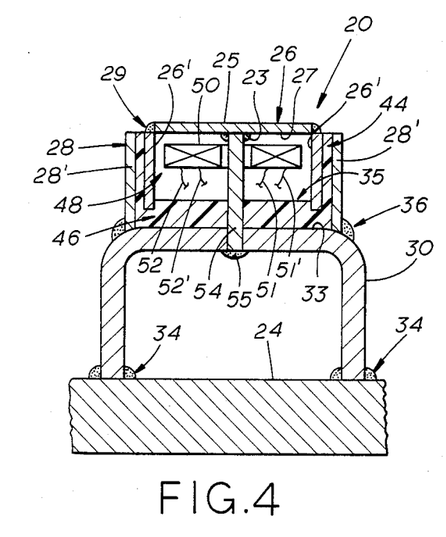
FIG. 4 is a vertical cross-sectional view of the current density monitoring apparatus taken along lines 4—4 of FIG. 3.
Figure 5:
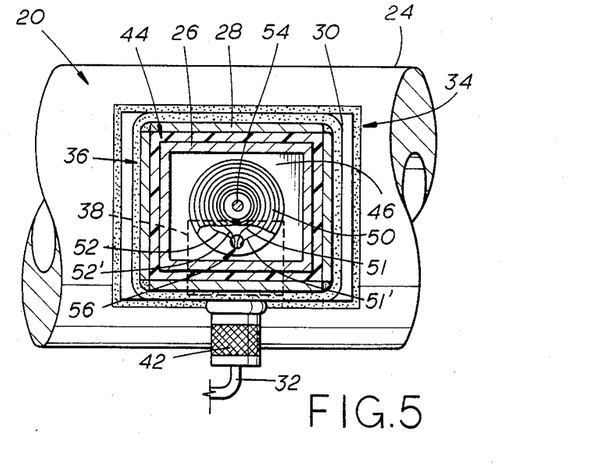
FIG. 5 is a horizontal cross-sectional view of the current density measuring apparatus taken along lines 5—5 of FIG. 2.

A saturable toroidal core 50 having an associated sensing coil is disposed in the interior of the inverted box section of sample cathode 26 and encircles the cathode connector rod 54. The toroidal core 50 has input exitation leads thereto 51—51', and output signal leads therefrom identified at 52—52'. As may be seen, the combination of the cathode connector rod 54 and the attached mounting bracket 30 form a connecting means that is substantially IR free for completing a direct electrical path between the sample cathode 26 and the metal structure 24. While it is impossible to provide an electrical connection that has zero resistance, a proper selection of ferrous metals can yield a connecting means having a combined resistance on the order of 5.0–8.9×10$^{-6}$ ohms. With the small current under investigation, say in the 0–5 mA range, accurate measurements of the current can be made.

A plastic sealing material is poured into the box-like housing 28 to a level 35 that rises above the ends of the sample cathode inverted walls 26' to form a sealing layer 46 and is then permitted to cure. The pouring of the plastic material 46 to the predetermined level 35 forms a fluid-tight, sealed chamber 48 within the confines of the inverted box-like sample cathode 26. The chamber is in direct contact with the inner surface 27 of the sample cathode and includes the toroidal core 50 and a portion of the rod 54. The remaining spaces between the walls 28' of the box-like housing member 28 and the spaced walls 26' of the sample cathode 26 are filled with the same plastic sealing material to form a sealing and insulating barrier 44 therebetween. Accordingly, the chamber 48 disposed within the housing member 28 is effectively fluid-tight and sealed from the electrolytic medium in which the current density monitoring device 20 is immersed.

The sealing barrier 44 provides a pressure seal to avoid incursion of the electrolytic medium, i.e., sea water, between the walls 28' of the housing 28 and the walls 26' of the sample cathode 26. The conductors 51, 51', 52 and 52' from the toroidal core 50 pass through an aperature 56 disposed in the upper surface 33 of mounting bracket 30 and into a sealed cable connector housing or junction box 38 that is mounted on the underside of the bracket 30 by suitable means such as brazing or welding at 40. The connector housing 38 coooperates with a high pressure cable connector 42 to provide a cable 32 that can be electrically connected to the toroidal core 50 with the instrument 20 in position on the structure 24.

It has been found that a preferred toroidal core 50 for use in the current density measurement according to this invention is a non-intrusive current measuring device such as a saturable toroidal core dc current sensor designated as a Series 903 Sensor and manufactured by American Aerospace Controls, Inc. Of course, other non-intrusive current measuring means may be utilized that can detect very low amperage dc currents and provide a uniformly linear dc output voltage directly proportional to the measured dc current across the entire range of the coil. In actual practice, the input current ranges vary upon application, and ranges of 0–5 mA, 0–10 mA, 0–20 mA, 0–50 mA, 0–100 mA, 0–200 mA, and 0–500 mA, and 0–1 amp are available, all providing a linear dc voltage output of 0–5 Vdc over the calibrated range of the device.

The sample cathode 26 is constructed of a material as nearly identical to that of the metal structure 24, and can be treated with the same coating or corrosion inhibiting paints or primers as is the surface of metal structure 24, in order that the surface 25 of sample cathode 26 presents as closely identical a surface as the surface of the metal structure 24. In addition, the sample cathode 26 may be constructed to be geoemtrically configured for accurately matching the geometry of the metal structure surface 24 at the location at which the sample cathode measuring device 20 is mounted.

Figure 6:
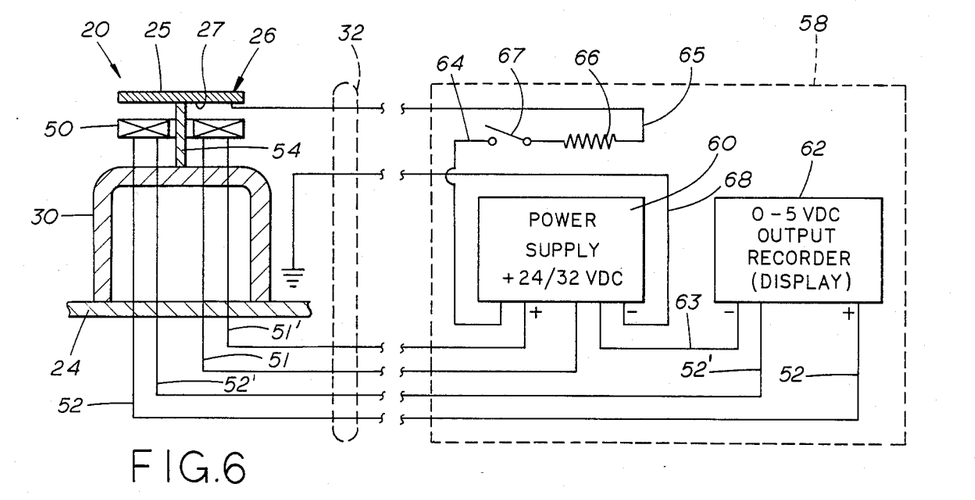
FIG. 6 is a schematic representation of the current density measuring apparatus and electrical circuitry associated therewith, including an optional modification for periodically de-polarizing the sample cathode surface.

A schematic diagram of the electrical circuitry associated with the current density measuring device 20 is shown in greater detail in FIG. 6. Current density measuring device 20 is shown only in structural schematic form, with the sample cathode 26 shown connected by means of the cathode connector rod 54 to the mounting bracket 30, which is in turn attached to the surface of metal structure 24. The toroidal core 50 is disposed around the cathode connector rod 54. A remote monitoring station, such as above sea level on the platform, has provided thereon a +24/32 Vdc power supply 60 and a 0–5 Vdc output recorder and/or display unit 62. Exitation voltage is applied to the toroidal core 50 from power supply 60 through conductors 51—51', and the voltage output corresponding to the measured current passing through rod 54 is applied through conductors 52 and 52' as inputs to the recorder and/or display unit 62. Conductor 63 interconnects the negative terminals of power supply 60 and the unit 62.

When excited by the power supply 60, the toroidal core 50 is saturated, and the changes in the magnetic flux field caused by the current flowing through sample cathode 26, cathode connector rod 54 and mounting bracket 30 into the metal structure 24, is sensed by the current sensing means 50 and generates an output voltage signal directly proportional to the detected and measured current flowing through the cathode connecting rod 54. This generated dc voltage signal is recorded and/or displayed by the output recorder and/or display unit 62 for purposes of recording the actual measured current density.

The toroidal core 50 can precisely measure, down to the range of 0–5 mA, current passing through the cathode connector rod 54, and generates a 0–5 Vdc linear output signal directly proportional to the measured current. Knowing the precise area of the sample cathode in contact with the electrolytic medium, the recorder or display unit 62 can be calibated to provide a direct, precise reading of current density. It has been found that in almost all applications, a cathode surface area in the range of 0.01 to 1.00# ft$^2$ is preferred. Accordingly, if the full scale input range of the current sensing toroidal core 50 is a 0–5.0 mA (generating a linear full scale 0–5.0 Vdc output), then it can be seen that if the measured current is 1.0 mA and the surface area of the sample cathode 26 is precisely 0.10 ft$^2$, then a Vdc voltage output signal is proportional to and representative of a 10.0 mA/ft$^2$ current density in the actual metal structure 24.

In utilizing a dc current in the cathodic protection system, a steady state condition develops where the cathode becomes polarized by hydrogen ions which form on the surface of the cathode and raise the impedance of the cathode. It is desirable to have the facility to "depolarize" the sample cathode periodically. As shown in FIG. 6, a depolarizing option is included, in which the positive output of power supply 60 is connected by conductor 64 to a switch 67 and a resistor 66 and conductor 65 to the inner surface 27 of the sample cathode 26. The negative output of power supply 60 is applied through conductor 63 to a grounded point on the cathodically protected metal structure 24. By periodically closing the switch 67, power supply 60 supplies a depolarizing current in a reverse direction to sample cathode 26, thus driving current from the sample cathode surface 25 in contact with the sea water. The repolarization of the cathode can then be examined to determine the efficiency of the cathodic protection system. Of course, all of the conductors from the remote monitoring station 58 to the current density measuring device 20 are carried thorugh cable 32 as previously described.

Figure 7:
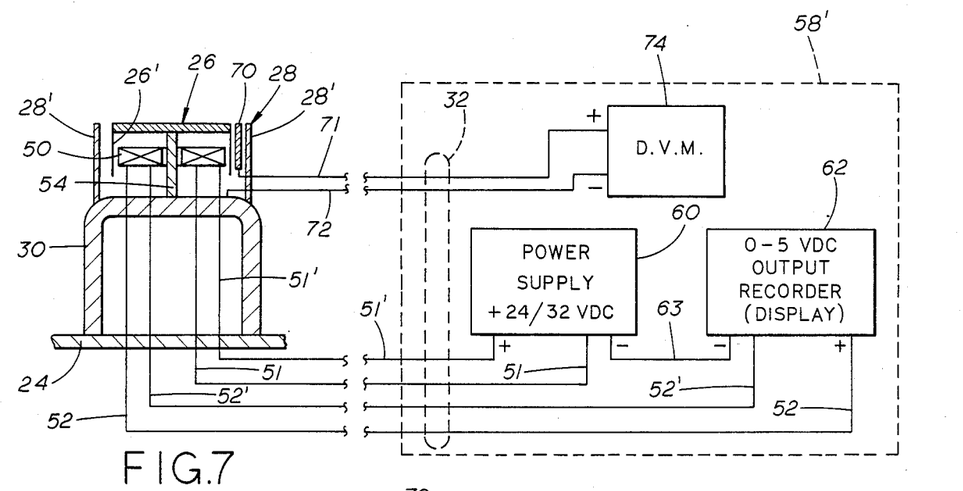
FIG. 7 is a schematic representation of the current density measuring apparatus according to the present invention showing another embodiment including a standard reference electrode disposed adjacent to the sample cathode for obtaining a reference electrode voltage potential in addition to the direct current density measurement.

In FIG. 7, another embodiment of the current density mesuring device 20 is shown, along with its associated circuitry. The current density monitoring device 20 is shown in general mechanical schematic form, and includes the sample cathode 26, disposed and sealed within the boxlike housing member 28, as hereinbefore described. However, the box-like housing member 28 is enlarged to accommodate between the walls 28' of the housing member 28 and the inverted walls 26' of the sample cathode structure 26 a standard reference electrode 70. The standard reference electrode 70 is usually constructed of a standard reference metal, such as zinc, silver—silver chloride, copper—copper sulphate or standard calomel.

At the remote monitoring station 58', the identical +24/32 Vdc power supply 60 and the 0-5 Vdc output recorder and/or display unit 62 is provided, as hereinabove described with regard to FIG. 6. The exitation voltage from power supply 60 is applied to core 50 by means of conductors 51—51', and the coil output voltage proportional to the current density is applied from coil 50 to the recorder and/or display unit 62 through conductors 52—52'. The negative outputs of the power supply 60 and the recorder 62 are commonly connected by means of a conductor 63. The function of the power supply 60 and the output recorder and/or display unit 62 is identical that hereinabove described with reference to FIG. 6, and will not be further described herein.

A digital voltmeter 74, located at the remote monitoring station 58', has its positive input applied through conductor 71 to the standard reference electrode 70, and its negative terminal is attached through conductor 72 to the mounting bracket 30, which forms a part of the substantially IR free connection means. The polarity of the hookup from the terminals of the voltmeter 74 to the reference electrode 70 may be reversed, depending on the reference electrode selected. The digital voltmeter will display the measured voltage potential difference between the reference electrode 70 and the metal structure 24 as measured through bracket 30 for providing reference electrode information in monitoring the efficiency and effectiveness of the cathodic protection system.

Figure 8:
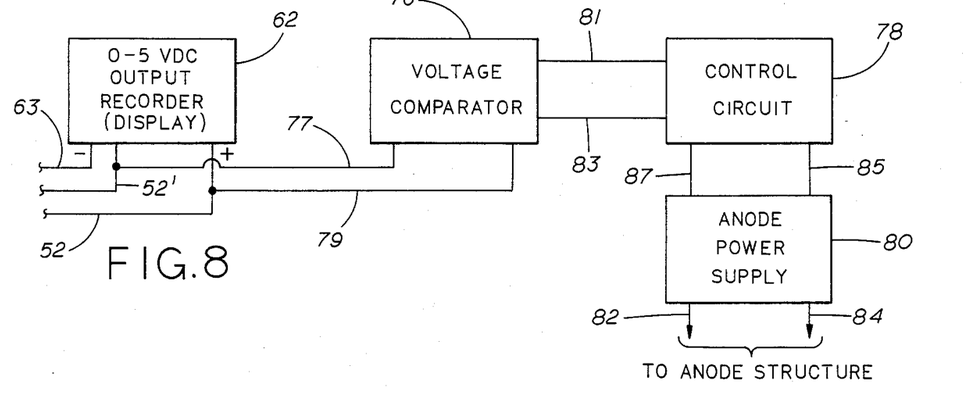
FIG. 8 is a block-diagram schematic of a control circuit for controlling the power supply of the cathodic protection systems anodes in response to the current density measurement.

In FIG. 8, a control circuit is shown schematically in block-diagram form for utilizing the voltage signal output of the toroidal core 50, representative of the current density applied to the sample cathode, and utilizing that voltage to control anode current provided by the anodes in the cathodic protection system. In FIG. 8, the 0-5 Vdc output recorder and/or display unit 62, identical to the units hereinabove discussed, is shown receiving the voltage outputs from core 50 through conductors 52 and 52'. The toroidal core 50 output voltage is also applied to a voltage comparator 76 through conductors 79 and 77 that are connected to recorder input conductors 52 and 52', respectively. The voltage comparator 76 detects the voltage signal level representative of the current density received through conductors 77 and 79 and detects predetermined changes between selected threshold levels in the voltage output signal which would correspond to predetermined or selected changes in the levels of the current density received by the sample cathode. If the threshold levels are exceeded, the comparator 76 would apply an appropriate signal through conductors 81 and 83 to a control circuit 78, which in turn would control the output of the anode power supply 80 by means of appropriate control signals applied thereto through conductors 85 and 87.

The control circuit 78 would direct the anode power supply 80 to either increase or decrease the current applied to the anode structure (not shown), thereby changing the current impressed on the metal structure 24 by the cathodic protection system, and changing the current density measured by sample cathode 26. In this way, the current applied to the structure can be controlled within predetermined limits or ranges in order to achieve optimum cathode current density and efficiency in response to the actual measured current at the sample cathode 26. The function of the voltage comparator 76 can be accomplished by means of a conventional operational amplifier circuit that will generate an output signal in response to the received signal exceeding (or falling below) a preselected level. The function of the control circuit 78 may be accomplished by a conventional rectifier control circuit generating appropriate control signals for application to the anode power supply 80.

Figure 9:
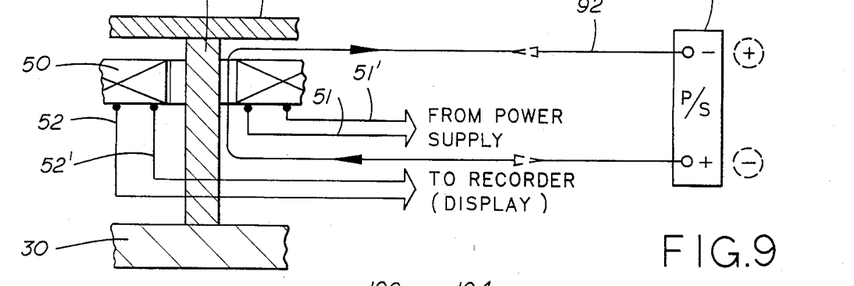
FIG. 9 is a schematic representation showing an embodiment for extending the range of the current density measuring apparatus and for calibrating the measuring circuit.

FIG. 9 shows another modification to the circuitry of the current density monitoring means 20 for special applications to extend the measurement range of the toroidal core 50 in certain applications, and to provide a means for calibrating the output of the core 50. By inserting a single conductor loop 92 inside of the coil 50 adjacent and between the coil 50 and the cathode connector rod 54, and by connecting the conductor loop 92 to a reversible power supply 90, the range of the core 50 output signals on conductors 52 and 52' may be extended and calibrated to actual conditions.

If the power supply 90 is attached to the loop conductor 92 to cause the current to flow in the direction as shown by the solid arrowheads, then the current in the loop is opposing the direction of current flow in the connector rod 54 as shown by the solid arrow pointing downwardly in the cathode connector rod, and the current sensed by the toroidal core 50 will be the difference of:

$$I(54) - I(92) = I(50)$$

Accordingly, the range of the toroidal coil 50 can be extended by applying a predetermined current through the conductor loop 92 in order to reduce the actual current detected by coil 50, but proportional to the actual current value. Multiple loops can be inserted for multiplying the effect of the reverse current flow and greatly extending the input range of the core 50.

For calibration purposes, the reversible power supply 90 would have its polarity reversed and current would flow in conductor loop 92 as shown by the dotted arrowheads in FIG. 9. In this configuration, the current in the loop would be reinforcing the direction of current flow in the cathode connector rod 54, and the current sensed in the toroidal coil 50 will be the addition of:

$$I(54) + I(92) = (50)$$

Accordingly, if the coil is reading a voltage output that corresponds to 2.5 mA, and if a 2.5 mA current is applied through conductor loop 92, then the resultant output voltage at conductors 52—52' should reflect a voltage signal directly representative of a 5.0 mA measured current. If the actual voltage measurement varies from that value, then the core 50 output voltage can be calibrated to provide a voltage that is exactly representative of the 5.0 mA current, thereby calibrating the output voltage of the core to correspond to the actual conditions.

Figures 10, 11:
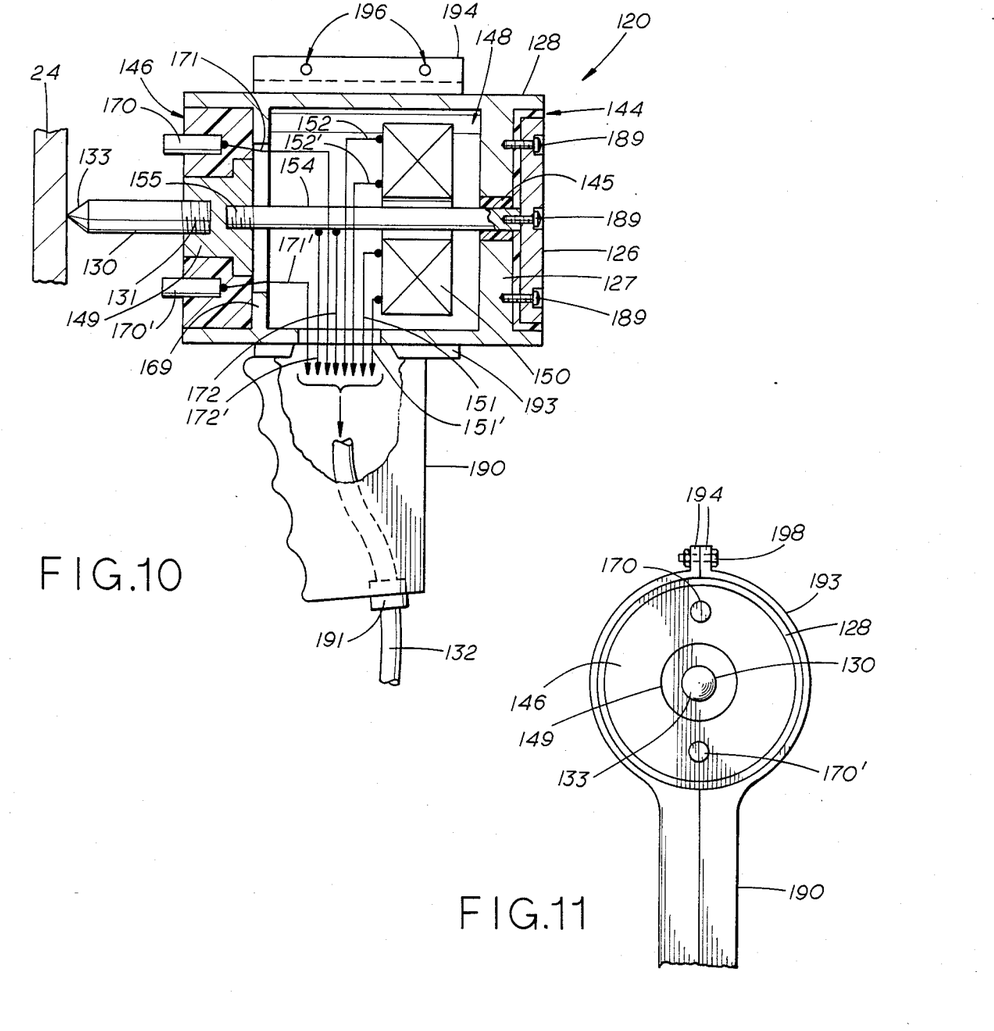
FIG. 10 is a vertical cross-sectional view of another embodiment of the current density measuring apparatus showing the apparatus contained in a portable, hand-held unit that may be used to measure current density at any desired location on the surface of a sub-sea metal structure.
FIG. 11 is a front view in elevation of the portable, hand-held current density measuring apparatus as shown in FIG. 10.

Referring now to FIGS. 10 and 11, a portable submarine current density monitoring device 120 is disclosed. The submarine portable measuring device 120 may be diver-held or submarine mounted for use in making current density measurements at selected remote locations on a sub-sea structure that were not equipped with current density monitoring devices 20 when the structure was installed, or to act as a back up or double check of the standard current density measuring means 26. A disc-shaped sample cathode 126 is constructed of a like metal to the metal of the structure 24 which is being cathodically protected. Portable measuring device 120 has a generally cylindrical housing 128 that has disposed adjacent one end an integral annular plate 127 with an aperature or opening axially therethrough. The other end of the generally cylindrical housing 128 has an annular ring 169 integrally disposed adjacent the opposite open end of the housing 128.

In the space between the annular plate 127 and the annular ring 169, a saturable toroidal core 150 is disposed and oriented to allow passage therethrough of a cathode connector rod 154. One end of the cathode connector rod 154 is attached to the center of the annular sample cathode plate 126, and in direct electrical contact therewith, by means of a detachable fastener such as a screw or a bolt 189. The other end 155 of connector rod 154 is attached in direct electrical contact to a mounting core 149 by any suitable means, such as welding, brazing, or, in order to make the mounting core 149 detachable, end 155 of rod 154 may be screw-threaded and threadably connected to corresponding and mating threads in core 149.

Sample cathode 126 is seated into the one end of the portable unit 120 against the annular plate 127 and sealed and insulated therefrom by means of insulating, packing or sealing means or material 144. The sample cathode 126 may be secured to the annular plate 127 by means of suitable fastening means, such as bolts or screws 189. A sealing and insulating plug 145 is secured around the end of the cathode connector rod 154 in contact with sample electrode 126. The plug 145 seals the aperature through the annular member 127, through which the rod 154 passes, to insure a fluid-tight closure of the sample cathode end of the generally cylindrical housing 128.

The other end of the housing 128 is closed by means of high pressure sealing and insulating material 146 forming an annular ring sealingly engaging the mounting core 149 and seating against the annular ring 169 to effectively create a fluid-tight seal of the other end of the housing 128. This sealing of both ends of the housing 128 creates a sealed chamber or cavity 148 within housing 128 through which a portion of the connector rod 154 passes, and which houses the saturable toroidal core 150.

A removable metal probe 130 may be detachably mounted to the core member 149 by means of mating screw threads 131. The probe terminates in a conically shaped tip 133 (or any other desirable tip geometry), that is adapted for contacting the surface of the metal structural member 124 for completing a substantially IR free connection between the sample cathode 126 and structure 24 through the cathode connector rod 154, core member 149, probe body 130, and probe tip 133.

The toroidal core 150 is provided with a pair of exitation voltage inputs 151 and 151', which function identically to the exitation inputs 51 and 51' as hereinabove previously described. The toroidal core 150 voltage output signals are applied through conductors 152 and 152', in a manner identical to that hereinabove described with regard to conductors 52 and 52' in previous embodiments. The portable monitoring device may also include at least one or more reference electrodes 170 and 170' disposed in the annular ring of sealing and insulation material 146. Conductors 171 and 171' interconnect to electrodes 170 and 170' and are directed through the cable 132, along with respective corresponding conductors 172 and 172' that are attached at one end to the cathode connector rod 154 for measuring the voltage potential between the reference electrodes 170 and 170' and the metal structure 24 as hereinabove described with regard to the embodiment disclosed in FIG. 7.

The portable unit 120 may be furnished with a handle 190 that is fluid-tight for preventing sea water from entering the handle and intruding into the interior of the housing member 128. Water intrusion could occur through aperatures (not shown) used for conveying the electrical circuit conductors via cable 132 from the interior of the housing 128 into handle 190. The cable 132 passes through a high-pressure seal 191 to a remote location carrying a power supply and an output recording and/or display unit, possibly identical to those hereinabove described with regard to power supply 60 and output recorder unit 62. The handle 190 also includes a bracket member 193 that mates with and surrounds the cylindrical housing member 128 and may terminate at the top thereof in a pair of opposing mating flanges 194 which are secured together by means of appropriate fasteners 198 through aperatures 196. In other embodiments, the power supply and voltage readout could be supplied internally of housing 128 in order that the person operating the hand-held unit can observe the readouts directly at the remote location, without the need for the cable from the unit to a remote location.

As may be seen, the structure and function of the hand-held device 120 closely parallels the structure and operation of the permanently mounted unit 20. The substantially IR free electrical connecting means comprises the cathode conductor rod 154, connecting block 149 and the probe 130. The probe tip 133 functions as a contacting means to complete the electrical path between the sample cathode 126 and the metal structure 24, similar to the function of the mounting bracket 30 in the mounted unit 20.

Figure 12:
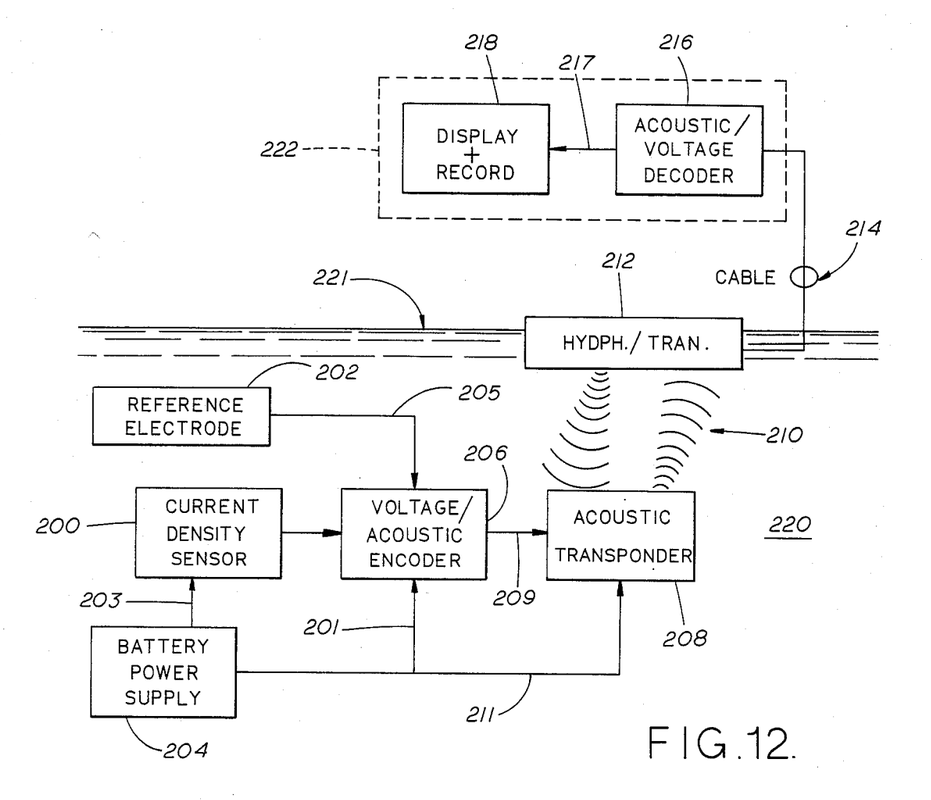
FIG. 12 is a block-diagram schematic of a transmission system for monitoring the current density measurement and reference electrode potential on a sub-sea structure in which the measurements are converted to acoustic signals and transmitted through the sea water to a remote location for detection.

FIG. 12 discloses in a block-diagram schematic an embodiment of an acoustic transmission system for obtaining and transmitting current density measurement and reference electrode voltages from a sub-sea location and acoustically transmitting the information to a receiving hydrophone in the sea water for detecting the acoustic signals and routing them to a remote location above sea level for conversion of the acoustic signals to voltage signals and displaying and recording of the current density and reference electrode information. The current density measuring device 200, voltage/acoustic encoder 206 and the acoustic transducer 208 are supplied with power from a sub-sea battery power supply 204 through conductors 203, 211 and 201, and 211 alone, respectively. The voltage output signal of the reference electrode is applied at 205 to a voltage/acoustic encoder 206, as is the current density measurement voltage signal which is applied via 207 to the voltage/acoustic encoder 206.

The voltage levels representative of the reference electrode potential and the current density in the structure are converted to acoustic signals which are coupled at 209 to an acoustic transponder 208. The acoustic transponder transmits the acoustic signals representative of the reference electrode potential and the measured current density via acoustic signals 210 through the ocean body 220 from the remote sub-sea location upon interrogation by the surface transducer/hydrophone 212.

The hydrophone or other acoustic sensing device 212 is disposed near the surface 221 of the sea 220, and detects the acoustic signals from transponder 208. Cable 214 is routed to an acoustic/voltage decoder 216 where the acoustic signals are reconverted into voltage levels representative of the reference electrode potential and the measured current density and applied at 217 to display and recording equipment 218. The acoustic voltage decoding unit 216 and the display and recording equipment 218 will be located above sea level at a remote location 222 for monitoring the cathodic protection system information. The topside equipment may be fixed or portable.

In a slightly different arrangement, the hydrophone would be dunked into or below the ocean surface 221 at periodic intervals and could send an acoustic interrogating command to the acoustic transducer 208 which would then transmit its acoustic information that had been stored from earlier readings, or which now commanded the sub-sea system to obtain the necessary measurements, and transmit the information via the acoustic transponder 208 for monitoring purposes.

Figure 13:
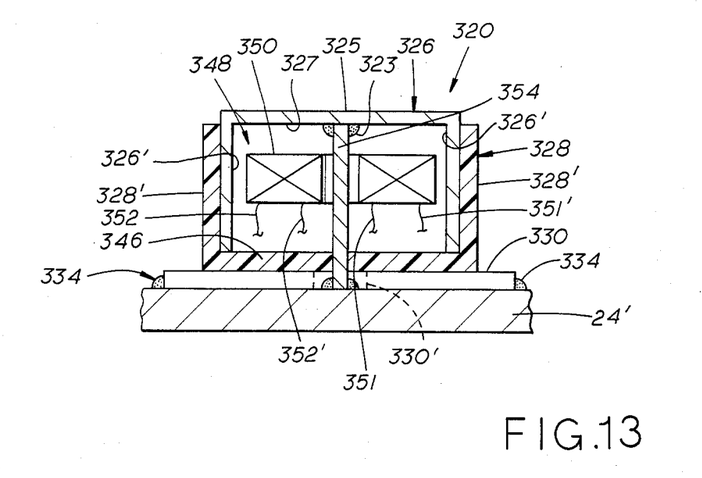
FIG. 13 is a vertical cross-sectional view of another embodiment of the current density monitoring apparatus according to the present invention more suitable for use in non-subsea applications.

Referring now to FIG. 13, another embodiment of the current measuring device 320 is disclosed, this device of a design that is generally suited for on-shore use as opposed to subsea use. The sample cathode 326 comprises a box-like structure having depending sidewalls 326' closed at the top by the sample cathode 326 with surface 325 in contact with the electrolytic medium, i.e., an earth formation, liquid in a storage tank, or the like. The sample cathode 326 forms an inverted box-like member open on the bottom side. A housing member 328 having side walls 328' is mounted on a pair of mounting brackets 330 and 330'. The brackets 330 and 330' may conveniently be formed in an "X" configuration to facilitate mounting on the metal structure 24' by means of welding or brazing as shown at 334. The housing walls 328' cooperate with a bottom part 346 to form the box-like housing member 328 having an open upper end.

The geometric configuration of the box-like housing member 328 is identical to the configuration of the inverted box-like sample cathode structure 326, but the walls 328' may be cast or formed directly on the walls 326' of the cathode means 326 to form a tight mechanical seal without the need for a separate seal disposed therebetween. In this embodiment, the housing 328 is constructed of an insulating material, such as the many plastic resin materials available, to insulate and seal the open end of the sample cathode inverted box-like structure 326 to form a sealed chamber 348. The housing 328 can be constructed of such materials in on-shore applications, since the devices 320 will not have to withstand the hydrostatic pressures of a subsea device 20 as hereinabove described.

A steel cathode connection rod 354 has one end connected to the inner surface 327 of the sample cathode 326 by means of brazing or welding 323. The other end of the cathode connector rod 354 is fixed to the mounting brackets 330 and 330'. A saturable toroidal core 350 having an associated sensing coil, identical in structure and function to the core 50 previously described, is disposed in the interior of the inverted box section of sample cathode 326 and encircles the cathode connector rod 354. The toroidal core 50 has input excitation leads thereto 351—351', and output signal leads therefrom identified at 352—352'.

The cavity 348 is effectively fluid-tight and sealed from the electrolytic medium in which the current density monitoring device 320 is immersed. The mechanical sealing barrier between walls 326' and 328' provides a seal to avoid incursion of the electrolytic medium, i.e., water or other electrolytic fluids, between the walls 328' of the housing 328 and the walls 326' of the sample cathode 326. The conductors 351, 351', 352 and 352' from the toroidal core 350 may be connected to a cable (not shown) similar to the cable 32 hereinabove previously described. The cathode connector rod 354 and the cross-mounting brackets 330 and 330' together form a substantially IR free connection between the sample cathode 326 and the protected metal structure 24'.

The function of the current measuring means 320 is identical to the operation and function of the device 20 hereinabove described in great detail. Similarly, any of the optional circuit arrangements shown in FIGS. 6 to 9 can be used with the measuring means 320 in the same manner in which it has been hereinbefore described in connection with the measuring device 20.

Numerous variations and modifications may be made in the structures herein described without departing from the present invention. Accordingly, it should be clearly understood that the form of the invention herein described and shown in the figures of the accompanying drawings are illustrative only and are not intended to limit the scope of the invention.

I claim:

1. Apparatus for directly measuring current density at the surface of a metal structure in contact with a surrounding electrolytic medium and protected by a cathodic protection system, comprising:

sample cathode means constructed of a like material as the metal structure and having a predetermined surface area exposed to the electrolytic medium and located adjacent the surface of the metal structure, connecting means that is substantially IR free for completing a direct electrical path between said sample cathode means exposed surface and the metal structure, housing means cooperating with at least said connecting means for forming a chamber sealed and insulated from the surrounding electrolytic medium and disposed between said sample cathode means and the metal structure with at least a portion of said connecting means passing through said sealed chamber, and current sensing means disposed within said sealed chamber and cooperating with at least a portion of said connection means passing therethrough for detecting the magnetic flux field associated with the current flow through said sample cathode means and said connecting means impressed by the cathodic protection system, said current sensing means generating an output voltage signal directly proportional to the detected current flow through said sample cathode means.

2. The apparatus of claim 1, where said sample cathode means comprises an inverted box-like member having one closed end and depending walls, said closed end forming the predetermined surface area in contact with the electrolytic medium, the open end of said box-like structure cooperating with said housing means to form said sealed chamber.

3. The apparatus of claim 2, where said housing means comprises a box-like member having one open end for sealingly receiving said inverted box-like sample cathode member therein for forming said sealed chamber therebetween.

4. The apparatus of claim 3, wherein said box-like housing member is constructed of a metallic material and the open end of said housing member is larger than the corresponding size of said sample cathode inverted box-like member for leaving a defined space therebetween and wherein said space is sealed by disposing a sealing material therein to seal the space between said sample cathode box-like member walls and said housing box-like member walls to form said sealed chamber therein.

5. The apparatus of claim 4, wherein said sealing material disposed between the walls of said sample cathode inverted box-like member and said housing box-like member fills the interior space of said housing box-like member to a level sufficient to engage the ends of said depending walls of said sample cathode inverted box-like member for forming said sealed chamber.

6. The apparatus of claim 1, wherein said connecting means comprises:
a cathode connector rod constructed of a metal providing a substantially IR free electrical path, one end of which is attached to said sample cathode means and in electrical contact therewith, and
contacting means cooperating with the other end of said cathode connector rod for establishing electrical contact with the surface of the metal structure to establish a substantially IR free electrical path between said sample cathode means and the metal structure.

7. The apparatus of claim 6, wherein a portion of said cathode connector rod interconnecting said sample cathode means and the metal structure passes through said sealed chamber.

8. The apparatus of claim 6, wherein said contacting means comprises a mounting bracket constructed of a metal providing a substantially IR free electrical path and fastened to the surface of the metal structure for making electrical contact therewith, said mounting bracket connected to said other end of said cathode connector rod in electrical contact therewith.

9. The apparatus of claim 8, wherein said mounting bracket is a generally inverted U-shaped member having the extending ends thereof welded to the metal structure, the upwardly extending closed section of said U-shaped bracket member having attached in electrical contact therewith said other end of said cathode connector rod.

10. The apparatus of claim 9, wherein the upwardly extending closed section of said generally U-shaped bracket member also mounts said housing means thereon.

11. The apparatus of claim 3, wherein said connecting means comprises:
a cathode connector rod constructed of a metal providing a substantially IR free electrical path, one end of which is attached in electrical contact with the interior surface of the closed end of the sample cathode inverted box-like member with at least a portion of said rod passing through said sealed chamber, and
contacting means cooperating with the other end of said cathode connector rod for establishing electrical contact with the surface of metal structure to establish a substantially IR free electrical path between said sample cathode surface and the metal structure.

12. The apparatus of claim 11, wherein said contacting means comprises a mounting bracket constructed of a metal providing a substantially IR free electrical path and fastened to the surface of the metal structure and making electrical contact therewith, said mounting bracket connected to said other end of said cathode connector rod in electrical contact therewith.

13. The apparatus of claim 12, wherein said mounting bracket is a generally inverted U-shaped member having the extending ends thereof welded to the metal structure, the upwardly extending closed section of said U-shaped bracket member having attached in electrical contact therewith said other end of said cathode connector rod.

14. The apparatus of claim 11, wherein said connector rod further functions to maintain said sample cathode member exposed surface in contact with the electrolytic medium in a fixed spaced relationship with respect to the closed end of said housing box-like member.

15. The apparatus of claim 1, wherein said sample cathode means comprises a disc-shaped member having one flat surface of predetermined area for contact with the electrolytic medium and a second flat mounting surface.

16. The apparatus of claim 15, wherein said housing means comprises:
generally cyclindrical body means having opposite open ends, one of said ends adapted to receive and and mount said disc-shaped sample cathode with said one flat surface of predetermined area facing outward in contact with the electrolytic medium, said disc shaped sample cathode closing said one end of said body means,
sealing means cooperating with said sample cathode member and said one end of said body means to seal said one end thereof,
means for removably attaching said sample cathodic member to said body means one end,
a disc-shaped closure means disposed in the open end of said body means and cooperating therewith to close and seal said other open end of said body means for forming a sealed chamber therein, said closure means having disposed therein an electrical current conducting element, and
a handle means attachable to and cooperating with said cyclindrical body means to form a handle for grasping and positioning said body means adjacent the metal structure.

17. The apparatus of claim 16, wherein said connecting means comprises:
a cathode connector rod constructed of a metal providing a substantially IR free electrical path, one end of which is attached to said sample cathode and in electrical contact therewith, and
contacting means cooperating with the other end of said cathode connector rod and said closure means for establishing electrical contact with the surface of the metal structure to establish a substantially IR free electrical path between said sample cathode member and said closure means.

18. The apparatus of claim 17, wherein a portion of said cathode connector rod interconnecting said sample cathode and said closure means passes through said sealed chamber.

19. The apparatus of claim 17, wherein said contacting means comprises an elongated metal probe constructed of a metal providing a substantially IR free electrical path, one end of which is removably attachable to said closure means and in electrical contact therewith, and the other end thereof terminating in a tip for establishing electrical contact with the metal structure when said tip is mechanically engaged therewith.

20. The apparatus of claim 3, wherein said box-like housing member is constructed of an electrical insulating material and is formed to sealingly engage said depending walls of said sample cathode box-like member to form said sealed chamber therein.

21. The apparatus of claim 1, wherein said current sensing means comprises a non-intrusive current measuring means disposed in said sealed chamber for measuring the current flowing through said connecting means as impressed on said sample cathode means by the cathodic protection system.

22. The apparatus of claim 21, wherein said non-intrusive current measuring means comprises:
a power supply for furnishing a predetermined exciting voltage,
a saturable toroidal core disposed in said sealed chamber and cooperating with said portion of said connecting means passing therethrough,
a cable electrically interconnecting said toroidal core and said power supply, and
said toroidal core in response to said exciting voltage detecting the magnetic flux field associated with the cathodic protection system current impressed on said sample cathode means and flowing through said connecting means, said toroidal core generating an output voltage signal directly proportional to the detected current.

23. The apparatus of claim 22, further including means interconnected to said toroidal core by said cable for receiving said toroidal core output voltage signal representative of said detected magnetic flux field and converting and displaying said signal as a direct representation of current density impressed on said sample cathode predetermined surface area exposed to the electrolytic medium.

24. The apparatus of claims 6 or 11 or 17, wherein said current sensing means comprises a non-intrusive current measuring means disposed in said sealed chamber for measuring the current flowing through said cathode connector rod as impressed on said sample cathode means by the cathodic protection system.

25. The apparatus of claim 24, wherein said non-intrusive current measuring means comprises:
a power supply for furnishing a predetermined exciting voltage,
a saturable toroidal core disposed in said sealed chamber and encircling said portion of said cathode connector rod passing therethrough, and
a cable electrically interconnecting said toroidal core and said power supply,
said toroidal core in response to said exciting voltage detecting the magnetic flux field associated with the cathodic protection system current impressed on said sample cathode means and flowing through said cathode connector rod, said toroidal core generating an output voltage signal directly proportional to the detected current.

26. The apparatus of claim 25, further including means interconnected to said toroidal core by said cable for receiving said core output voltage signal representative of said detected magnetic flux field and converting and displaying said signal as a direct representation of current density impressed on said sample cathode predetermined surface area exposed to the electrolytic medium.

27. The apparatus of claim 1, further including:
at least one reference electrode cooperating with said housing means and spaced from and electrically insulated from said sample cathode means for generating a reference voltage in response to the impressed cathodic protection system current, and
measuring means interconnected to said at least one reference electrode for measuring said generated reference voltage.

28. The apparatus of claim 1, further including:
a load resistor one side of which is connected to said sample cathode means,
a switch in series with said load resistor, and
a source of electrical power, the positive output of which is applied through said switch and said load resistor to said sample cathode means, the negative terminal of which is connected to said metal structure, for applying a predetermined depolarizing electrical voltage to said sample cathode means when said switch is closed.

29. The apparatus of claim 1, further including:
voltage comparator means for receiving said current sensing means output voltage signal representative of said detected sample cathode current and generating in response thereto an output voltage signal when said current sensing means output deviates from a preselected voltage level, and
control circuit means for receiving said voltage comparator means output signal and generating in response thereto output control signals for controlling the cathodic protection system anode power supply and changing the anode current impressed on the metal structure in response thereto.

30. The apparatus of claim 25, further including magnetic flux means for applying a magnetic flux field of predetermined polarity between said saturable toroiddal core and said cathode connection rod for changing the total magnetic flux field detected by said core and changing by a predetermined value the resultant toroidal core output voltage signal.

31. The apparatus of claim 30, wherein said magnetic flux means comprises:
at least one coil of an electrical conductor looped between said cathode connector rod and said core, and
a source of reversible electrical power interconnected to said conductor coil for applying an electrical curent of predetermined value in a first direction that is in the same direction as the current flow in said cathode connector rod for generating a magnetic flux field of a predetermined value additive to the magnetic flux field created by the cathodic protection system impressed current, and for applying an electrical current of predetermined value in a second direction that is opposite to the direction of current flow in said cathode connector rod for generating a magnetic flux field of predetermined value that opposes the magentic flux field created by the impressed current of the cathodic protection system.

32. The apparatus of claim 27, wherein said metal structure is located in a subsea environment, and said electrolytic medium is water, and wherein said apparatus further comprises:

voltage/acoustic encoding means located adjacent the metal structure in the subsea environment and receiving the output voltage signals from said current sensing means and said reference electrode means for converting said voltage signals to encoded acoustic signals, transponder means located in the subsea environment for receiving said encoded acoustic signals from said voltage/acoustic encoding means and transmitting said acoustic signals through the water medium, a battery power supply located in the subsea environment for powering said current sensing means, voltage/acoustic encoding means and said acoustic transponder means, a hydrophone located near the water surface and remote from said transponder means for receiving said acoustic signals transmitted through the water by said transponder means, acoustic/voltage decoding means located remotely from said transponder means for receiving the acoustic signals from said hydrophone and converting said received coded acoustic signals to voltage signals representative of the current density and the reference electrode potential, and means for measuring and displaying said voltage signals representative of current density and the reference electrode potential.

33. The apparatus of claim 32, wherein said hydrophone also includes an acoustic tranponder for transmitting an acoustic interrogation signal in the water medium, and wherein said transponder means also includes an acoustic receiver means for receiving said interrogation signal from said hydrophone and in response thereto transmitting said encoded acoustic signals representative of said reference electrode means potential and said current density.

34. Apparatus for directly measuring current density at the surface of a metal structure in contact with a surrounding electrolytic medium and protected by a cathodic protection system, comprising:

a sample cathode member constructed of a like material as said metal structure, and having an inverted box-like configuration with one closed end and depending walls, said closed end forming a sample cathode of predetermined area in contact with the electrolytic medium, a housing member having a box-like configuration with one open end for sealingly receiving said inverted box-like sample cathode member therein and forming a chamber there-between sealed from the surrounding electrolytic medium, a cathode connector rod constructed of a metal providing a substantially IR free electrical path, one end of which is attached to said sample cathode member surface opposite the surface in contact with the electrolytic medium and in electrical contact therewith, contacting means cooperating with the other end of said cathode connector rod for establishing electrical contact with the surface of the metal structure to establish a substantially IR free electrical path between said sample cathode member and the metal structure, at least a portion of said rod passing through said sealed chamber, and current sensing means disposed within said sealed chamber and cooperating with at least a portion of said cathode connector rod passing therethrough for detecting the magnetic flux field associated with the current flow through said sample cathode member and said cathode connector rod impressed by the cathodic protection system, said current sensing means generating an output voltage signal directly proportional to the detected current flow through said sample cathode member.

35. The apparatus of claim 34, wherein said box-like housing member is constructed of a metallic material and the open end of said housing member is larger than the corresponding size of said sample cathode inverted box-like member for leaving a defined space therebetween, and wherein said space is sealed by disposing a sealing material therein to seal and insulate the space between said sample cathode box-like member walls and said housing box-like member walls to form said sealed chamber therein.

36. The apparatus of claim 35, wherein said sealing material disposed between the walls of said sample cathode inverted box-like member and said housing box-like member fills the interior space of said housing box-like member to a level sufficient to engage the ends of said depending walls of said sample cathode inverted box-like member for forming said sealed chamber.

37. The apparatus of claim 34, wherein said contacting means comprises a mounting bracket constructed of a metal providing a substantially IR free electrical path for being fastened to the surface of the metal structure and making electrical contact therewith, said mounting bracket adapted for mounting said other end of said cathode connector rod in electrical contact therewith.

38. The apparatus of claim 37, wherein said mounting bracket is a generally inverted U-shaped member having the extending ends thereof welded to the metal structure, the upwardly extending closed section of said U-shaped bracket member having attached in electrical contact therewith said other end of said cathode connector rod.

39. The apparatus of claim 38, wherein the upwardly extending closed section of said generally U-shaped bracket member also mounts said housing means thereon.

40. The apparatus of claim 34, wherein said current sensing means comprises a non-intrusive current measuring means disposed in said sealed chamber for measuring the current flowing through said cathode connector rod as impressed on said sample cathode means by the cathodic protection system.

41. The apparatus of claim 40, wherein said non-intrusive current measuring means comprises:

a power supply for furnishing a predetermined exciting voltage, a saturable toroidal core disposed in said sealed chamber and cooperating with said portion of said cathode connector rod passing therethrough, and a cable electrically interconnecting said toroidal core and said power supply, said toroidal core in response to said exciting voltage detecting the magnetic flux field associated with the cathodic protection system current impressed on said sample cathode means and flowing through said cathode connector rod, said toroidal core generating an output voltage signal directly proportional to the detected current.

42. The apparatus of claim 41, further including means interconnected to said toroidal core by said cable for receiving said toroidal core output voltage signal representative of said detected magnetic flux field and converting and displaying said signal as a direct representation of current density impressed on said sample cathode surface of predetermined area exposed to the electrolytic medium.

43. The apparatus of claim 34, further including:
at least one reference electrode cooperating with said housing member and spaced and electrically insulated from said sample cathode member for generating a reference voltage in response to the impressed cathodic protection system current, and
measuring means interconnected to said at least one reference electrode for measuring said generated reference voltage.

44. The apparatus of claim 34, further including:
a load resistor one side of which is connected to said sample cathode member,
a switch in series with said load resistor, and
a source of electrical power, the positive output of which is applied through said switch and said load resistor to said sample cathode member, the negative terminal of which is connected to said metal structure for applying a predetermined depolarizing electrical voltage to said sample cathode member when said switch is closed.

45. The apparatus of claim 34, further including:
voltage comparator means for receiving said current sensing means output voltage signal representative of said detected sample cathode current and generating in response thereto an output voltage signal when said current sensing means output voltage signal deviates from a preselected voltage level, and
control circuit means for receiving said voltage comparator means output signal and generating in response thereto output control signals for controlling the cathodic protection system anode power supply and changing the anode current impressed on the metal structure in response thereto.

46. The apparatus of claim 34, further including magnetic flux means for applying a magnetic flux field of predetermined value and polarity between said saturable toroidal core and said cathode connector rod for changing the total magnetic flux field detected by said toroidal core by said predetermined value and changing by a predetermined value the resultant toroidal core output voltage signal.

47. The apparatus of claim 46, wherein said magnetic flux means comprises:
at least one coil of an electrical conductor looped between said cathode connector rod and said core, and
a source of reversible electrical power interconnected to said conductor coil for applying an electrical current of predetermined value in a first direction that is in the same direction as the current flow in said cathode connector rod for generating a magnetic flux field of a predetermined value additive to the magnetic flux field created by the cathodic protection system impressed current, and for applying an electrical current of predetermined value in a second direction that is opposite to the direction of current flow in said cathode connector rod for generating a magnetic flux field of a predetermined value that opposes the magnetic flux field created by the impressed current of the cathodic protection system.

48. A method of directly measuring current density at the surface of a metal structure in contact with a surrounding electrolytic medium and protected by a cathodic protection system, comprising the steps of:
locating adjacent the surface of the metal structure a sample cathode constructed of a like material as the metal structure and having a predetermined surface area exposed to the electrolytic medium,
completing a direct electrical path that is substantially IR free between said sample cathode exposed surface and the metal structure,
insulating from the surrounding electrolytic medium between said sample cathode and the metal structure at least a portion of said electrical path passing therethrough,
detecting the magnetic flux field associated with the current flow through said sample cathode and said insulated portion of said connecting electrical path impressed by the cathodic protection system and generating a signal directly proportional to the detected current flow through said sample cathode and said insulated portion of said connecting electrical path, and
determining the current density impressed upon said sample cathode in a direct relationship to said measured current.

49. The method of claim 48, further including the step of visually displaying a representation of the direct measurement of said current density.

50. The method of claim 48, further including the step of depolarizing said sample cathode by periodically impressing on said sample cathode a reverse polarity voltage for a predetermined time period.

51. The method of claim 48, wherein said detecting and generating steps are performed by a saturable toroidal core which has impressed thereon a predetermined exitation voltage.

52. The method of claim 48, further including the step of determining the voltage potential between an electrode constructed of a standard reference electrode metal disposed adjacent said sample cathode.

53. The method of claim 48, further including the step of controlling the anode power supply of the cathodic protection system in response to said generated voltage signal representative of said current density.

54. The method of claim 51, wherein the range of magnetic flux density sensed by said toroidal core may be extended by adding the following steps:
disposing at least a single loop of a conductor between said toroidal core and said substantially IR free electrical path, and
impressing a current flow of a predetermined value through said conductor loop in a direction opposite to the direction of the current flow through said substantially IR free electrical path for generating a reverse magnetic flux field of predetermined value that cancels at least a portion of the magnetic flux field associated with current flow through said substantially IR free electrical path.

55. The method of claim 54, wherein the output voltage of said coil associated with said toroidal core may be calibrated by the step of impressing a current flow of a predetermined value through said conductor loop in the same direction as the direction of current flow through said substantially IR free electrical path for generating a reinforcing magnetic flux field of predetermined value that adds to the magnetic flux field associated with current flow through said substantially IR free electrical path.

56. The method of claim 48, wherein the metal structure is located in a subsea location, and further including the additional steps of:

converting said generated voltage signals representative of measured current density to acoustic signals representative of said measured current density, and transmitting said acoustic signals representative of measured current density through the sea water.

57. The method of claim 56, further including the steps of:

detecting said transmitted acoustic signals in the sea water at a location remote from the transmitting location, converting said detected acoustic signals to voltage signals representative of said current density, and transmitting said voltage signals representative of said measured current density to a location above sea level and remote from said acoustic transmitting location.

* * * * *